US006851448B2

United States Patent
Fujii

(12) United States Patent
(10) Patent No.: US 6,851,448 B2
(45) Date of Patent: Feb. 8, 2005

(54) ROTARY CONNECTOR WITH VALVE

(75) Inventor: Ryoji Fujii, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 0 days.

(21) Appl. No.: 10/471,486

(22) PCT Filed: Mar. 13, 2002

(86) PCT No.: PCT/JP02/02389
§ 371 (c)(1),
(2), (4) Date: Sep. 11, 2003

(87) PCT Pub. No.: WO02/075200
PCT Pub. Date: Sep. 26, 2002

(65) Prior Publication Data
US 2004/0089348 A1 May 13, 2004

(30) Foreign Application Priority Data
Mar. 21, 2001 (JP) ........................................ 2001-080600

(51) Int. Cl.[7] ............................ F16L 37/28; F16K 15/14
(52) U.S. Cl. ...................... 137/515; 137/846; 285/921
(58) Field of Search .............................. 137/515, 515.5, 137/515.7, 843, 846; 285/921

(56) References Cited
U.S. PATENT DOCUMENTS 996,588 A * 6/1911 Kennedy .................. 137/515.7
4,143,853 A * 3/1979 Abramson ................ 251/149.1
5,218,993 A * 6/1993 Steinberg et al. ......... 137/515.5
6,453,941 B1 * 9/2002 Milhas et al. ................ 137/515

FOREIGN PATENT DOCUMENTS

| JP | 63-44638 | 11/1988 |
|---|---|---|
| JP | 2-114288 | 9/1990 |
| JP | 3-126466 | 5/1991 |

* cited by examiner

Primary Examiner—Ramesh Krishnamurthy
(74) Attorney, Agent, or Firm—Merchant & Gould P.C.

(57) ABSTRACT

A rotary connector with valve, comprising first and second connector members (1, 2) having connector terminal parts (5, 6) and fitting parts (7, 8) with hollows (3, 4) as fluid passages formed therein and a valve member (12), wherein the first and second connector members are rotably connected to each other by fitting the fitting parts thereof to each other and the valve member is stored in a valve storage part (11) formed in the fitting part, valve pressing parts (14, 15) are provided on the first and second connectors (1, 2) on the side of the valve storage part, and at least a part of the valve member is pressingly held between the both valve pressing parts to hold a sealability, and a frictional force acting between the both valve pressing parts and the valve member is set so as to come within such a range that the first and second connector members can be rotated each other, whereby a structure allowing an easy assembly and an absorption of the twist of a line can be provided.

9 Claims, 3 Drawing Sheets

ROTARY CONNECTOR WITH VALVE

TECHNICAL FIELD

The present invention relates mainly to connectors used in infusion lines, and more particularly to valved rotary connectors that are provided with a one-way valve or the like that is used in order to prevent backflow.

BACKGROUND ART

For conventional valved connectors, there are those of the male/female type and the tube-bonded type. In the male/female type, a main body having a valve-seating portion in which a valve is disposed is provided with a male or a female connector portion. The tubes to be connected are provided with corresponding female or male connectors, and connection is established by coupling the male and female connector portions together. It is possible to employ various structures for coupling the two, and ordinarily it is necessary that the two can be rotated relatively to one another, as in a screw-type connection. With such a male/female connector, the member to be connected can be attached or detached as necessary. In the case of the tube-bonded type, a tube is directly bonded to a tube-shaped linking portion provided on a member for seating a valve, thereby coupling them together. Consequently, the coupling is permanent.

When using such a conventional valved connector, relative rotation is impossible at the coupling portion between connector and tube in a state in which the tube line is connected by the connector. Consequently, when the tube is twisted, the rotational torque acts on the tube, whereby obstruction of the flow path in the tube or damage to the tube may be caused.

Moreover, in the case of a male/female connector, when the tube is twisted in a state in which the tube line is connected, the screwing of the screw-joint portion may be loosened, and in some cases it even may be dislodged.

Furthermore, in the case of twisting the tube-bonded connectors, there is no loosening or dislodging of the connection, but it cannot be avoided that the flow path in the tube is obstructed or that the tube is damaged. Furthermore, in tube-bonded connectors there is the problem that it is not possible to rearrange the line, and that the setup is bothersome.

DISCLOSURE OF THE INVENTION

It is an object of the present invention to present a valved connector that can be assembled easily, with which reassembly of the line is possible, so that it is easy to alter or adjust the direction of an infusion port or a branching means such as a three-way stopcock provided in a line, and with which twisting of the line can be absorbed, so that the possibility of loosening or disconnection as well as the load on the tube can be reduced.

A rotary connector with valve according to a basic configuration of the present invention includes a first and a second connector member each having a fitting portion and a connector portion provided with an inner bore serving as a liquid flow path, and a valve member arranged in the liquid flow path. The first and the second connector member are coupled rotatably to one another by fitting the fitting portions together, and the valve member is seated in a valve-seating portion formed in the fitting portions. The fitting portions of the first and the second connector members are provided with respective valve-pressing portions facing the valve-seating portion, and, by clamping and pressing at least a portion of the valve member between the two valve-pressing portions, liquid-tightness is preserved between the inner bore and the outside of the connector at a location at which the two fitting portions are coupled. Moreover, a pressing force with which the two valve-pressing portions act on the valve member is set such that a frictional force exerted between the two valve-pressing portions and the valve member is in a range that allows the first connector member and the second connector member to rotate relatively to one another.

With this configuration, the first connector member and the second connector member can be rotated relatively to one another while preserving liquid-tightness, so as to absorb twisting of the tube as well as the rotational torque acting on the tube and the object to be connected.

In this configuration, it is preferable that at least one of the connector portions of the first and second connector members has a structure with which objects to be connected can be engaged by mutual rotation. Moreover, the pressing force acting on the valve member is set such that the torque for rotating the first connector member and the second connector member relatively to one another against the frictional force exerted between the two valve-pressing portions and the valve member is smaller than the torque necessary to dislodge the engagement of the objects to be connected and the connector portion. Thus, the effect of absorbing the twisting of the tube can be ensured without loosening the engagement between the connector portion and the objects to be connected.

In the above configuration, it is preferable that the valve member has a base portion that is substantially cylindrical and inside of which a valve is formed, and a flange formed at one end thereof The valve-seating portion is formed in one of the fitting portions, and has a substantially circular cavity that is coaxial with the inner bore and a large diameter portion that is provided at an aperture end of the cavity, and an end face that is formed by a step between the large diameter portion and the cavity and that is perpendicular to the inner bore, which acts as one of the valve-pressing portions. An end face of the fitting portion that is not provided with the valve-seating portion acts as the other valve-pressing portion. The flange is clamped and pressed between the two valve-pressing portions. With this configuration, the effect of the present invention can be attained in a form that is suitable to the structure of connectors.

In the above configuration, it is preferable that the fitting portion that is not provided with the valve-seating portion has a valve-holding portion that protrudes in an axial direction towards the valve-seating portion on an inner peripheral side of the end face forming the valve-pressing portion, and protrusion of the valve member toward the inner bore is prevented by the valve-holding portion. That is to say, when the flange is clamped by the valve-pressing surfaces, the connector members rotatively slide with respect to the valve member, and thus there is the risk that a force acts on the flange in the direction causing the valve member to slip from between the valve-pressing surfaces into the inner bore, but with this configuration such slipping can be prevented.

In the above basic configuration of the present invention, it is preferable that the valve member has a base portion that is substantially cylindrical and inside of which a valve is formed. The valve-seating portion is formed in one fitting portion, and has a substantially circular cavity that is coaxial with the inner bore, an inner peripheral surface at an end portion thereof acting as a valve-pressing portion. The fitting portion that is not provided with the valve-seating portion has a cylindrical protrusion portion that is linked to the inner bore, an outer peripheral surface of the cylindrical protrusion acting as a valve-pressing portion. A cylindrical end portion of the base portion of the valve member is clamped and pressed between the two valve-pressing portions. With this configuration, the effect of the present invention can be attained in a form that is suitable to the structure of connectors.

In the above configuration, it is preferable that both of the two valve-pressing portions have a ring-shaped rib, and the ring-shaped ribs are arranged in opposition to one another, such that they abut against the valve member. With this configuration, liquid-tightness can be preserved reliably, and both thread portions can be rotated with a small torque.

It is preferable that dimensions of the ribs are set such that an amount of the valve member deformed by pressure is in a range of 10 to 70% of the valve member's wall thickness. It is further preferable that this range is 30 to 60%.

In the above configurations, the valve member seated in the valve-seating portion may be a one-way valve member.

BEST MODE FOR CARRYING OUT THE INVENTION

Embodiment 1

Figure 1:
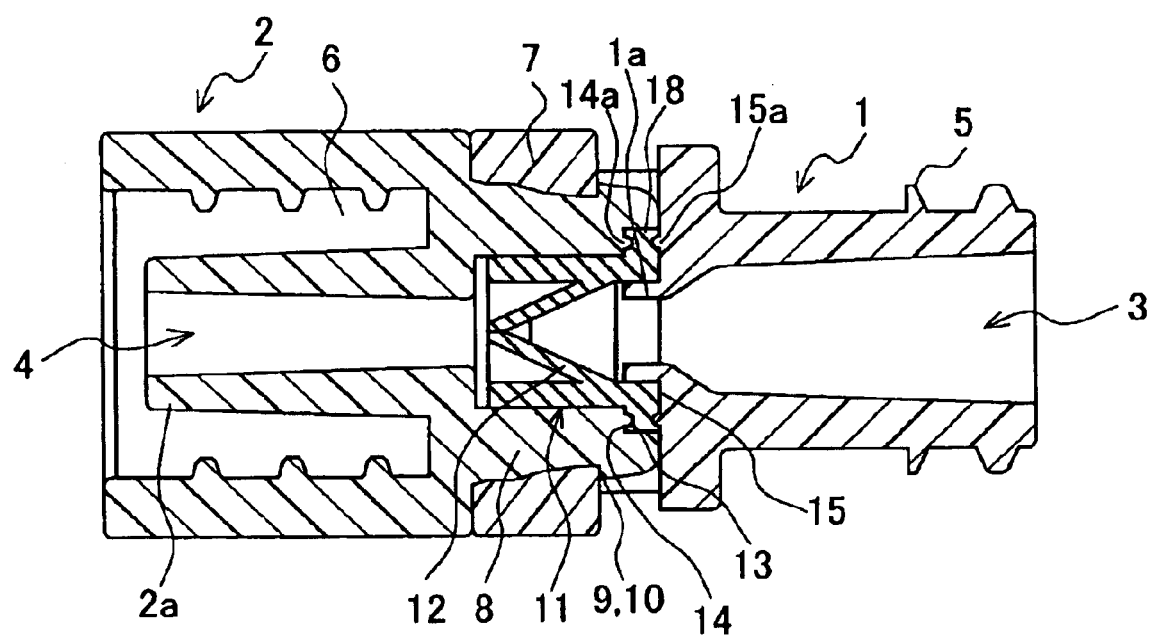
FIG. 1 is a sectional view showing a connector with one-way valve according to Embodiment 1 of the present invention.

FIG. 1 is a sectional view showing a connector with valve according to Embodiment 1. This connector is made of a first connector member 1 and a second connector member 2. The first connector member 1 and the second connector member 2 both have an inner bore 3, 4 serving as the flow path for a liquid. A male thread 5 serving as a connector portion is formed on the outer surface of the first connector member 1, and a female thread 6 serving as a connector portion is formed on the inner surface of the second connector member 2.

The inner bore 3 of the first connector member 1 at the end having the male thread 5 is formed in a tapered shape, so that a luer-type end portion can be inserted and fitted. Also the inner bore 4 formed at an inner tube portion 2a of the second connector member 2 is formed in a tapered shape.

The first connector member 1 has an outer fitting portion 7 (as shown clearly in FIG. 2B, which is explained below). The second connector member 2 has an inner fitting portion 8 whose outer diameter is smaller than the inner diameter of the outer fitting portion 7. Consequently, the first connector member 1 and the second connector member 2 can be coupled by inserting the inner fitting portion 8 into the outer fitting portion 7 and fitting the two together. The outer fitting portion 7 and the inner fitting portion 8 have a step portion 9, 10, and by engaging these step portions 9 and 10, the first connector member 1 and the second connector member 2 are interlocked such that they are not inadvertently dislodged. The inner diameter of the outer fitting portion 7, the outer diameter of the inner fitting portion 8, and the positions of the step portions 9 and 10 are set such that the first connector member 1 and the second connector member 2 can be rotated relatively to one another around the axis of the male thread 5 and the female thread 6.

A valve-seating portion 11 is formed inside the inner fitting portion 8 of the second connector member 2. In this embodiment, a one-way valve member 12 is seated in the valve-seating portion 11.

The first connector member 1 and the second connector member 2 can be made of a plastic material, and are preferably made using a transparent plastic material. The one-way valve member 12 is made of an elastomer with little elution, excellent abrasion resistance and low compressive permanent set, such as silicone rubber.

Figure 2B:
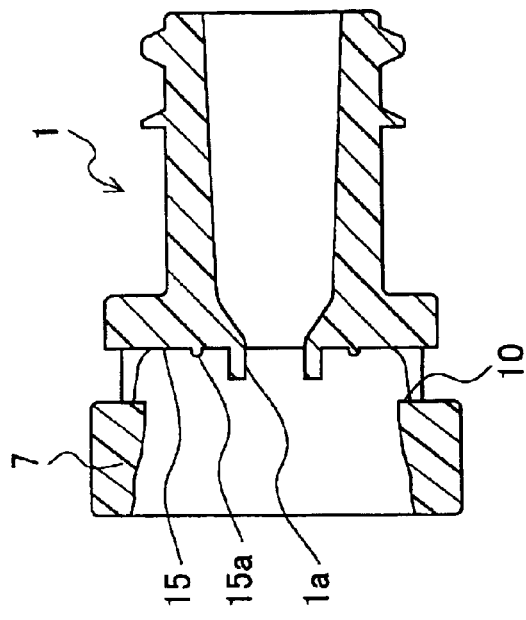
FIG. 2B is a sectional view showing a first connector member of the connector with one-way valve in FIG. 1.
Figure 2C:
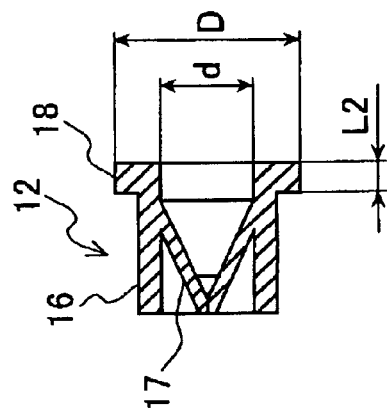
FIG. 2C is a sectional view showing a one-way valve member constituting the connector with one-way valve in FIG. 1.
Figure 2A:
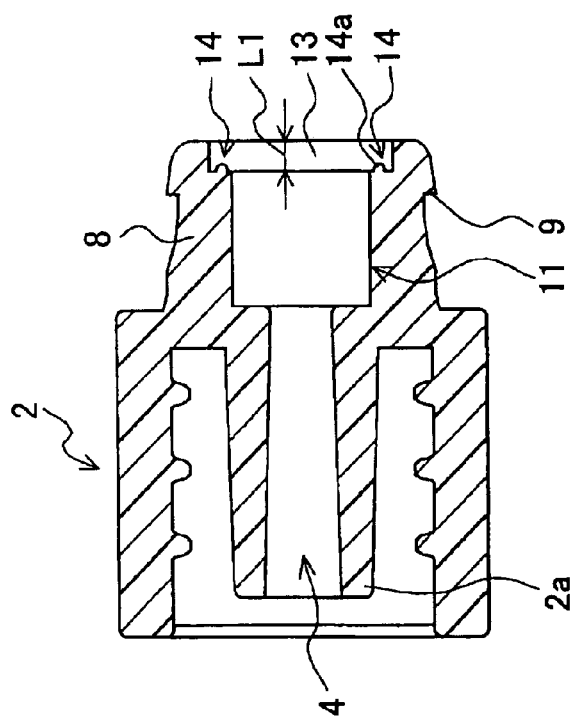
FIG. 2A is a sectional view showing a second connector member of the connector with one-way valve in FIG. 1.

FIG. 2 shows sectional views in which the connector of FIG. 1 has been taken apart. FIG. 2A shows the second connector member 2, FIG. 2B shows the first connector member 1, and FIG. 2C shows the one-way valve member 12. As shown in FIG. 2A, the valve-seating portion 11 includes a circular cavity, and has a large diameter portion 13 on its aperture end. L1 denotes the length of the large diameter portion 13 in the axial direction. A ring-shaped rib 14a is formed at a valve-pressing surface 14 that is formed by a step between the large diameter portion 13 and the circular cavity.

The inner end surface of the outer fitting portion 7 of the first connector member 1 shown in FIG. 2B constitutes a valve-pressing surface 15, which opposes the valve-pressing surface 14. Also the valve-pressing surface 15 is provided with a ring-shaped rib 15a, similar to the rib 14a. The rib 14a and the rib 15a are arranged such that they are in opposition to one another when the first connector member 1 and the second connector member 2 are coupled. A substantially cylindrical valve-holding portion 1a is formed on the inner side of the outer fitting portion 7.

As shown in FIG. 2C, the one-way valve member 12 has a substantially cylindrical base portion 16, and a one-way valve 17 is formed inside of it. At one end, a flange 18 is formed. L2 denotes the length of the flange 18 in the axial direction, d denotes the inner diameter of the flange 18, and D denotes its outer diameter. The length and the outer diameter of the base portion 16, and the outer diameter D of the flange 18, should be dimensioned such that the one-way valve 12 fits into the valve-seating portion 11.

In the state in which the connector is assembled as shown in FIG. 1, the valve-pressing surface 14 at the large diameter portion 13 of the second connector member 2 and the valve-pressing surface 15 at the first connector member 1 clamp the flange 18 of the one-way valve member 12, and the flange 18 is pressed from both sides. In this situation, the flange 18 of the one-way valve member 12 is deformed by the opposing ribs 14a and 15a. Thus, an adequate pressing force is produced between the ribs 14a, 15a and the one-way valve member 12. Consequently, the connection portion of the inner bores 3 and 4 serving as the flow path for the liquid is sealed, and a liquid-tight portion functioning to prevent leaks is formed. Thus, not only is liquid-tightness preserved, but the pressure force is adjusted by suitably setting the dimensions of each member, and the friction force acting between the valve-pressing surfaces 14, 15 and the one-way valve member 12 is restricted to a range in which the first connector member 1 and the second connector member 2 can be rotated relatively to one another. More specifically, it is set such that the first connector member 1 and the second connector member 2 can be rotated relatively to one another with a torque that is smaller than the torque that is necessary to unscrew the member that is screw-jointed with the male thread 5 or the female thread 6.

It should be noted that when the flange 18 is clamped by the valve-pressing surfaces 14 and 15, there is the risk that when rotatively sliding the connector member relatively to the one-way valve member 12, a force is applied to the flange 18 from between the valve-pressing surfaces 14 and 15 in the direction in which the flange 18 slips (slides) into the inner bore. The valve-holding portion la has the function to counter this force and to hold the flange 18 between the valve-pressing surfaces 14 and 15.

Due to this action of the valve-pressing surfaces 14 and 15, the first connector member 1 and the second connector member 2 can be rotated relatively to one another while maintaining liquid-tightness, so that twisting of the tube or rotational torques acting on the tube or the connected object can be absorbed without loosening the screwing of the male thread and the female thread.

It should be noted that it is not essential to provide the ribs 14a and 14b, and it is also possible to employ a structure in which the valve-pressing surfaces 14 and 15 are pressed directly to the flange 18. However, providing the ribs 14a and 15a ensures liquid-tight operation and makes it possible to rotate both threaded portions with little torque.

The dimensions of the ribs 14a and 15a should be set such that a deformed amount of the flange 18 of the one-way valve member 12 is in the range of 10 to 70% of the thickness of the valve wall. More preferably, it is 30 to 60%. Consequently, in the range in which this condition is satisfied, the spacing between the rib 14a and the rib 15a should be smaller than the length L2 in the axial direction of the flange 18 of the one-way valve member 12. Therefore, the play for fitting the outer fitting portion 7 to the inner fitting portion 8 and the length L1 of the large diameter portion 13 of the valve-seating portion 11 should be set appropriately.

Embodiment 2

Figure 3:
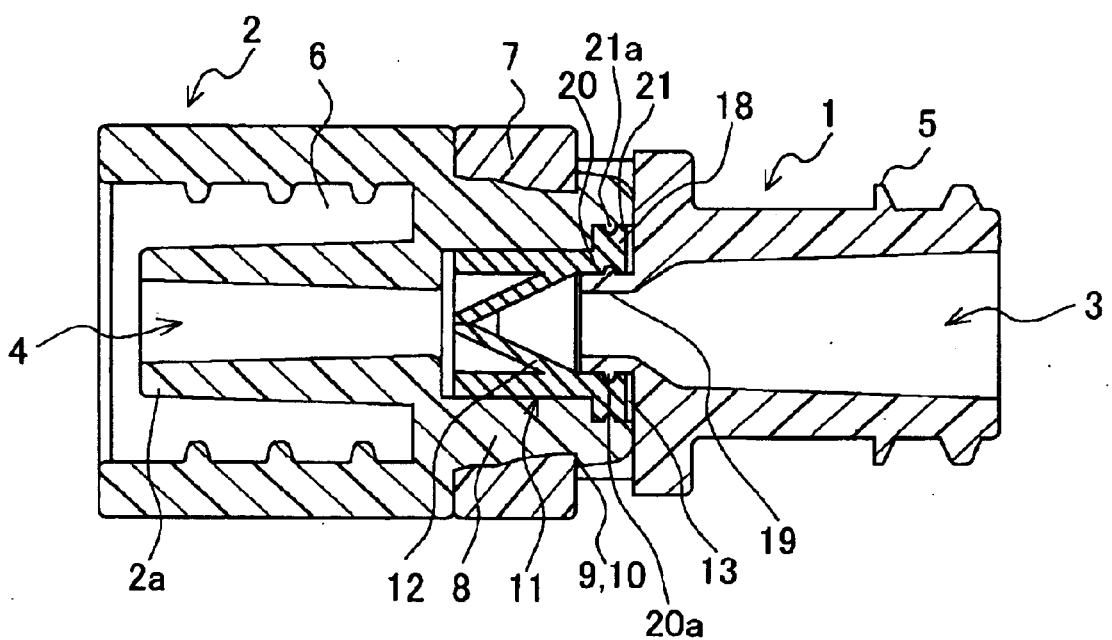
FIG. 3 is a sectional view showing a connector with one-way valve according to Embodiment 2 of the present invention.
Figure 4:
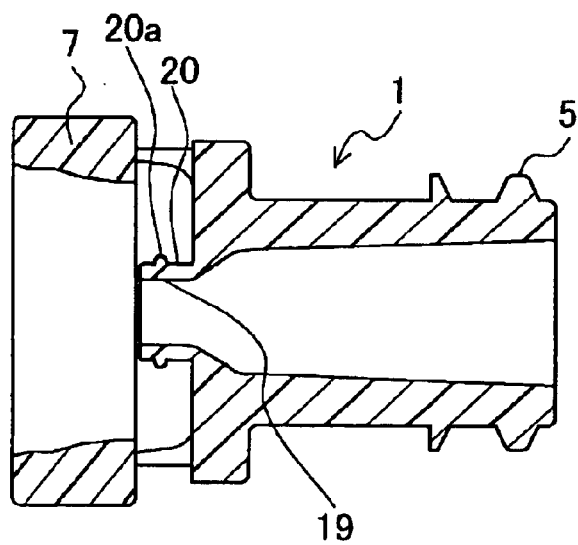
FIG. 4 is a sectional view showing a first connector member in the connector with one-way valve in FIG. 3.

FIG. 3 is a sectional view showing a connector with valve according to Embodiment 2 of the present invention. This embodiment differs from Embodiment 1 in the configuration with which the flange 18 of the one-way valve member 12 is pressed. The inner bore 3 of the first connector member 1 has a small diameter at the outer fitting portion 7, and is provided with a cylindrical protrusion 19. The outer peripheral surface of the cylindrical protrusion 19 constitutes an inner valve-pressing surface 20. The inner peripheral surface of the large diameter portion 13 of the valve-seating portion 11 constitutes an outer valve-pressing surface 21. The valve-pressing surface 20 and the valve-pressing surface 21 are in opposition, and the flange 18 of the one-way valve member 12 is clamped in the ring-shaped space formed between them. The valve-pressing surfaces 20 and 21 are provided with ring-shaped ribs. 20a and 21a, respectively. It is preferable that the wall thickness (D–d)/2 of the flange 18 of the one-way valve member 12 is formed slightly larger than the spacing between the opposing ring-shaped ribs.

With this configuration, pressure is exerted on the inner peripheral surface and the outer peripheral surface of the flange 18 from the valve-pressing surface 20 and the valve-pressing surface 21, respectively. Moreover, a portion of the flange 18 of the one-way valve member 12 is deformed in the radial direction by the ring-shaped ribs 20a and 21a provided on the valve-pressing surfaces 20 and 21, similar to the effect of the ribs 14a and 16a in Embodiment 1, thus ensuring the effect of the valve-pressing surfaces for preserving liquid-tightness. However, the ring-shaped ribs are not required, and it is also possible to attain liquid-tightness when a structure without ribs is used.

The pressure force from the valve-pressing surfaces 20 and 21 is set such that the frictional force acting between the valve-pressing surfaces 20 and 21 and the one-way valve member 12 is restricted to a range in which the first connector member 1 and the second connector member 2 can rotate relatively to one another. More specifically, as in Embodiment 1, it is set such that the first connector member 1 and the second connector member 2 can be rotated relatively to one another with a torque that is smaller than the torque that is necessary to unscrew the member that is linked by the male thread 5 or the female thread 6.

Due to this effect of the valve-pressing surfaces 20 and 21, the first connector member 1 and the second connector member 2 can be rotated relatively to one another while maintaining liquid-tightness, so that twisting of the tube or rotational torques acting on the tube and the connected object can be absorbed without loosening the screwing of the male thread and the female thread.

It should be noted that this embodiment has been described for the case that the valve seated in the connector is a one-way valve, but the present invention can also be applied to connectors seating other types of valves.

Moreover, the structure of the connector portion provided at the first connector member 1 or the second connector member 2 is not limited to the male thread 5, the female thread 6 or tapered end portion as described above. That is to say, the present invention can be effectively applied to any structure in which coupling and decoupling an engagement is carried out by rotating relatively to one another.

INDUSTRIAL APPLICABILITY

A connector with valve according to the present invention can be assembled easily, makes it possible to reassemble the line, and, by absorbing twisting of the line, to reduce the possibility of loosening or dislodging and to reduce the load due to rotational torque acting on the tube or the connected object.

What is claimed is:

1. A rotary connector with valve, comprising a first and a second connector member each having a fitting portion and a connector portion provided with an inner bore serving as a liquid flow path, and a valve member arranged in the liquid flow path, wherein the first and the second connector member are coupled rotatably to one another by fitting the fitting portions together, wherein the valve member is seated in a valve-seating portion formed in the fitting portion;

wherein the fitting portions of the first and the second connector members are provided with respective valve-pressing portions facing the valve-seating portion, wherein, by clamping and pressing at least a portion of the valve member between the two valve-pressing portions, liquid-tightness is preserved between the inner bore and the outside of the connector at a location at which the two fitting portions are coupled; and wherein a pressing force with which the two valve-pressing portions act on the valve member is set such that a frictional force exerted between the two valve-pressing portions and the valve member is in a range that allows the first connector member and the second connector member to rotate relatively to one another.

2. The rotary connector with valve according to claim 1, wherein at least one of the connector portions of the first and second connector members has a structure with which objects to be connected can be engaged by mutual rotation, wherein the pressing force acting on the valve member is set such that the torque for rotating the first connector member and the second connector member relatively to one another against the frictional force exerted between the two valve-pressing portions and the valve member is smaller than the torque necessary to dislodge the engagement of the objects to be connected and the connector portion.

3. The rotary connector with valve according to claim 1, wherein the valve member has a base portion that is substantially cylindrical and inside of which a valve is formed, and a flange formed at one end thereof, wherein the valve-seating portion is formed in one of the fitting portions, and has a substantially circular cavity that is coaxial with the inner bore and a large diameter portion that is provided at an aperture end of the cavity, and wherein an end face that is formed by a step between the large diameter portion and the cavity and that is perpendicular to the inner bore acts as one of the valve-pressing portions;

wherein an end face of the fitting portion that is not provided with the valve-seating portion acts as the other valve-pressing portion; and wherein the flange is clamped and pressed between the two valve-pressing portions.

4. The rotary connector with valve according to claim 3, wherein the fitting portion that is not provided with the valve-seating portion has a valve-holding portion that protrudes in axial direction towards the valve-seating portion on an inner peripheral side of the end face forming the valve-pressing portion, and wherein protrusion of the valve member toward the inner bore is prevented by the valve-holding portion.

5. The rotary connector with valve according to claim 1, wherein the valve member has a base portion that is substantially cylindrical and inside of which a valve is formed;

wherein the valve-seating portion is formed in one fitting portion, and has a substantially circular cavity that is coaxial with the inner bore, an inner peripheral surface at an end portion thereof acting as a valve-pressing portion;

wherein the fitting portion that is not provided with the valve-seating portion has a cylindrical protrusion portion that is linked to the inner bore, an outer peripheral surface of the cylindrical protrusion acting as a valve-pressing portion; and wherein a cylindrical end portion of the base portion of the valve member is clamped and pressed between the two valve-pressing portions.

6. The rotary connector with valve according to claim 1, wherein both the two valve-pressing portions have a ring-shaped rib, and the ring-shaped ribs are arranged in opposition to one another, such that they abut against the valve member.

7. The rotary connector with valve according to claim 6, wherein dimensions of the ribs are set such that an amount of the valve member deformed by pressure is in a range of 10 to 70% of the valve member's wall thickness.

8. The rotary connector with valve according to claim 7, wherein the range is 30 to 60%.

9. The rotary connector with valve according to claim 1, wherein the valve member seated in the valve-seating portion is a one-way valve member.

* * * * *